United States Patent
Cheng et al.

(10) Patent No.: US 10,123,887 B2
(45) Date of Patent: Nov. 13, 2018

(54) VACUUM SUCTION AND PRESSURE REGULATION PNEUMATIC CYLINDER

(71) Applicant: KEN DALL ENTERPRISE CO., LTD., New Taipei (TW)

(72) Inventors: Chia-Pao Cheng, New Taipei (TW); Chih-Hsuan Liang, New Taipei (TW)

(73) Assignee: KEN DALL ENTERPRISE CO., LTD., New Taipei (TW)

( * ) Notice: Subject to any disclaimer, the term of this patent is extended or adjusted under 35 U.S.C. 154(b) by 207 days.

(21) Appl. No.: 15/381,127

(22) Filed: Dec. 16, 2016

(65) Prior Publication Data

US 2018/0168829 A1    Jun. 21, 2018

(51) Int. Cl.
*A61F 2/68* (2006.01)
*A61F 2/64* (2006.01)
*A61F 2/50* (2006.01)
*A61F 2/74* (2006.01)

(52) U.S. Cl.
CPC .................. *A61F 2/68* (2013.01); *A61F 2/64* (2013.01); *A61F 2002/5006* (2013.01); *A61F 2002/747* (2013.01); *A61F 2002/748* (2013.01)

(58) Field of Classification Search
CPC ...... F16F 7/02; F16F 7/003; F16F 9/06; F16F 6/02; A61F 2/68; A61F 2/64; F15B 15/149; F15B 15/22; F15B 15/227
See application file for complete search history.

(56) References Cited

U.S. PATENT DOCUMENTS

2018/0036149 A1*    2/2018  Harris .................... A61F 2/6607

* cited by examiner

*Primary Examiner* — Thomas E Lazo
*Assistant Examiner* — Daniel Collins
(74) *Attorney, Agent, or Firm* — Leong C. Lei

(57) ABSTRACT

A vacuum suction and pressure regulation cylinder includes a pneumatic cylinder, in which a fixed division plate is arranged. A piston assembly is slidably arranged in the fixed division plate and includes an airtight piston mounted to a middle portion thereof and including a flowrate regulation screw and an end of the piston assembly is provided with a second airtight piston so as to define, in an interior space of the pneumatic cylinder, a first air chamber, a second air chamber, and a third air chamber, which are in communication with a prosthesis sleeve. When the piston assembly moves, air flow induced in the pneumatic cylinder varies the sizes of the air chambers for regulation of the spaces thereof. Further, the variation of the air chambers helps evacuate the sleeve so as to make a stump and the prosthesis tightly coupled to each other through suction.

4 Claims, 12 Drawing Sheets

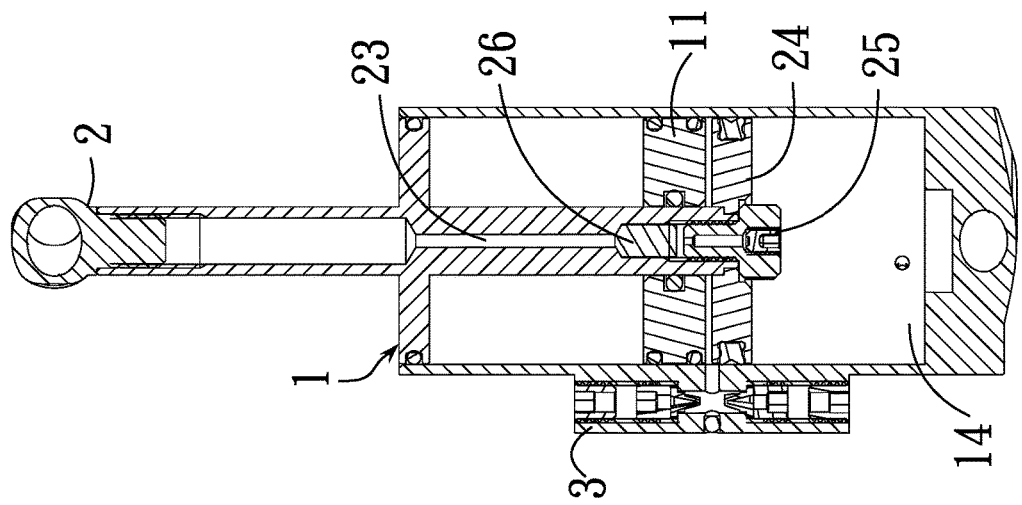
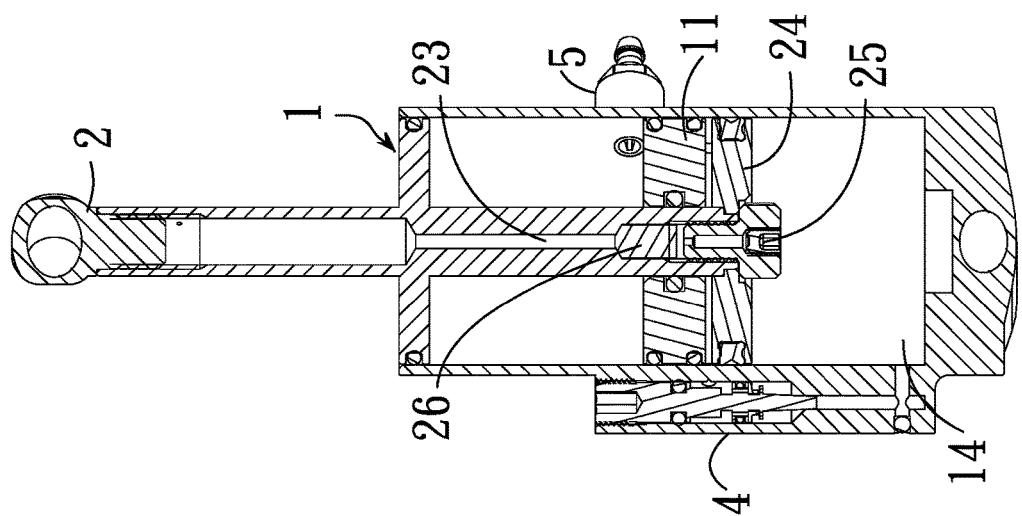
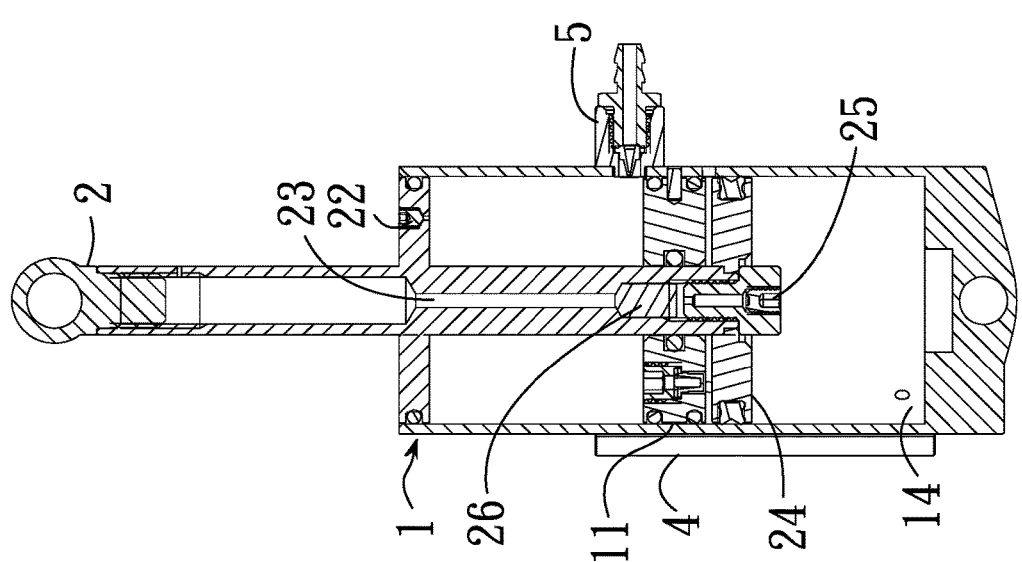

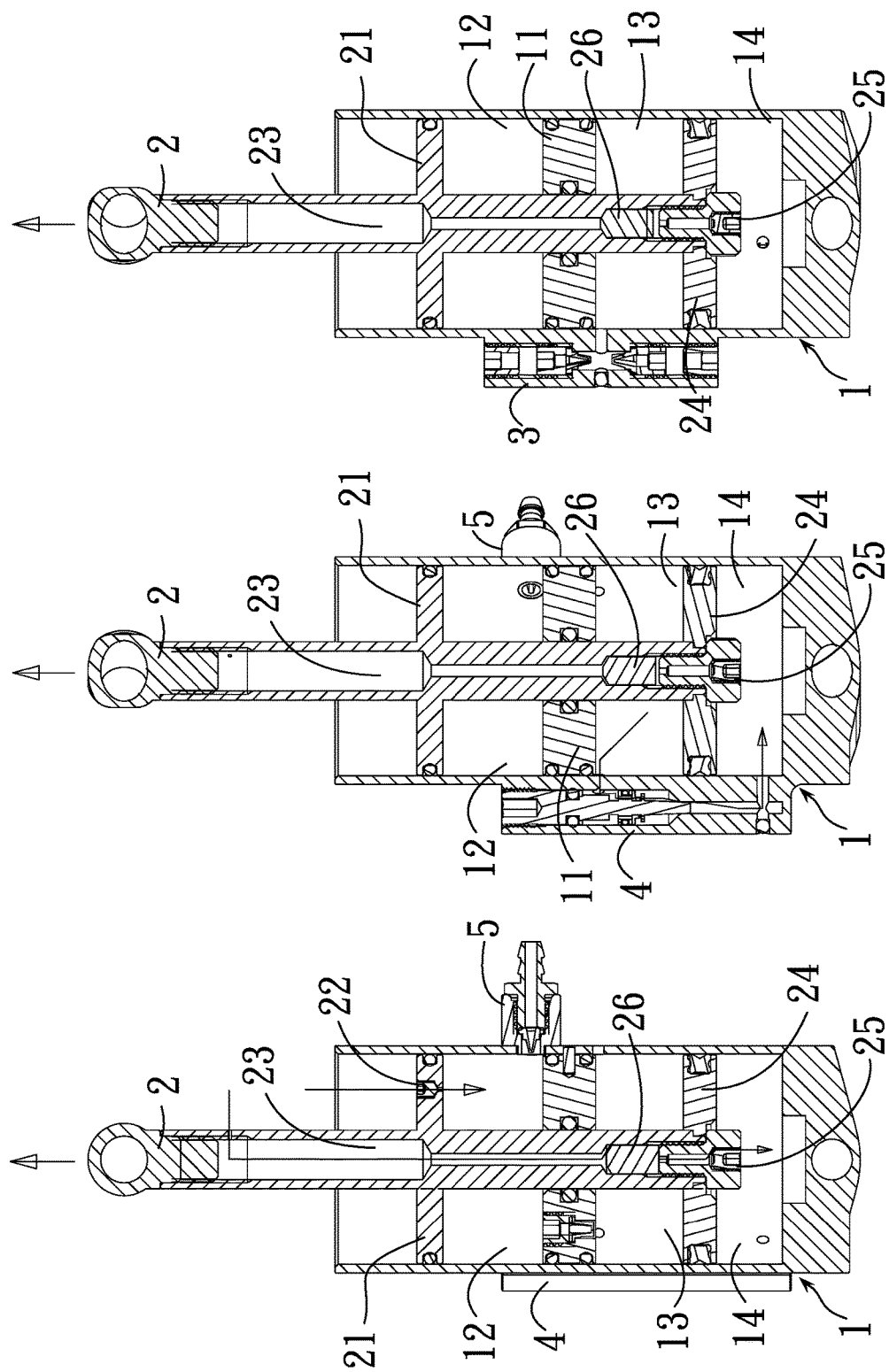

VACUUM SUCTION AND PRESSURE REGULATION PNEUMATIC CYLINDER

TECHNICAL FIELD OF THE INVENTION

The present invention relates to a cushioning pneumatic cylinder, and more particular to a vacuum suction and pressure regulation pneumatic cylinder for pressure cushioning of artificial knees, wherein a pneumatic cylinder comprises a plurality of air chambers arranged therein to allow for adjustment of volumes of the air chambers according to treading movements of a user so as to regulate vacuum degree of a sleeve, allowing the user to walk and march in a more natural style and also featuring security and safety.

DESCRIPTION OF THE PRIOR ART

With the progress of medical science and medical therapeutic techniques and practice, the application of pneumatic cylinders in artificial knees provides a very commonly acceptable medical measure. To fit the needs of installation and operation of a user, most of the commonly used pneumatic cylinders must be first tuned according to various factors, including the body size of the user and the habits and feeling of comfort of the user to provide the best perceptive result of the user in wearing and operating a prosthesis.

For walking in a high speed, insufficiency of internal cushioning pressure inside a pneumatic cylinder is often a reason that makes it not possible for achieving walking in a high speed. Further researches and studies by artisans in the field provide an improved structure of the pneumatic cylinder for improving and alleviating such a problem.

U.S. Pat. No. 9,180,026 discloses an adjustment-free cushioning air cylinder, in which an air chamber is formed in the air cylinder and a piston is arranged inside the air chamber to divide the air chamber into an upper chamber and a lower chamber. An end of the piston is located in the air chamber, while an opposite end is extended to the outside of the air chamber. A first check valve is mounted in the piston for connection between the upper chamber and the lower chamber so as to allow air to flow in a single direction from the upper chamber into the lower chamber. An upper air way is formed in the air cylinder and in communication with the upper chamber and the outside. A second check valve is arranged in the upper air way and the second check valve has an end in communication with the outside and an opposite end in communication with the upper chamber to allow air to flow, in a single direction, from the outside into the upper chamber. A lower air way is formed in the air cylinder and in communication with the lower chamber and the outside. The upper air way is made to have an inside diameter that is greater than an inside diameter of the lower air way so that an ingress air flow rate of the air chamber is greater than an egress air flow rate. As such, the complicated interior structure of a traditional air cylinder is thus improved and the advantage that air ingress is made in a one-way manner and is greater than air egress eliminates the need for periodical re-fill of air and allows for automatic regulation air ingress with the habit of walking of a user to overcome an issue of unexpected quick operations.

The known cushioning air cylinder as discussed above involves numerous improvements. However, the single feature that air ingress flow rate is greater than air egress flow rate may not fit for various operations by different users, who might have different styles of walking and may also not suit for different conditions of local areas, such as regular ground surfaces, stairways, uphill slopes, and mountain traces. Thus, an ultimate target of improvement would be being fit for different users having various habits and being suitable to operations in different local terrain conditions.

SUMMARY OF THE INVENTION

In view of the above problems, the present invention aims to improve the drawbacks of the prior art devices by providing a vacuum suction and pressure regulation pneumatic cylinder that specifically suits the needs of modern users.

The present invention provides a vacuum suction and pressure regulation cylinder, which comprises a pneumatic cylinder having an outer circumferential surface on which a first one-way valve, a second one-way valve, and a sleeve one-way valve are mounted and in communication with the interior thereof. The pneumatic cylinder is provided therein with a fixed division plate. A piston assembly is provided, at a middle portion thereof, with a first airtight piston that comprises a flowrate regulation screw. The piston assembly is slidably arranged in the fixed division plate so that the first airtight piston is hermetically enclosed in the pneumatic cylinder to define a first air chamber between the first airtight piston and the fixed division plate. The first air chamber is in communication with the sleeve one-way valve to draw air contained in a sleeve into the first air chamber. The piston assembly has an end to which a second airtight piston is mounted to define, in combination with the fixed division plate, a second air chamber. The second air chamber is in communication with the first one-way valve so as to allow the first one-way valve to draw in air outside the pneumatic cylinder. A third air chamber is defined between the second airtight piston and an internal bottom of the pneumatic cylinder. The second one-way valve is in communication with the second air chamber and the third air chamber. The piston assembly is provided with a piston air passage formed therein.

The vacuum suction and pressure regulation cylinder of the present invention makes use of the air chambers formed in the pneumatic cylinder to change sizes thereof with air flowing in the air chambers during a movement of the piston assembly in order to provide balance and regulation for walking. The air chambers are in communication with the sleeve so that when the piston assembly moves, the size variation of the air chambers helps evacuate the interior space of the sleeve, allowing a stump and a prosthesis sleeve to be tightly coupled through suction thereby greatly reducing the perception of weight of the prosthesis during walking. The piston air passage is provided therein with a floating piston and a flow reduction screw, so that the air contained in the third air chamber cannot be immediately discharged out at the moment when it is just compressed and a resistance may induced against air discharging to thereby provide a power for assisting fast walking and allowing a user to walk in a more natural style and making the use more comfortable.

The foregoing objectives and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

BRIEF DESCRIPTION OF THE DRAWINGS

FIGS. 5A, 5B, and 5C are cross-sectional views of the present invention respectively taken along line A-A of FIG. 4A, line B-B of FIG. 4B, and line C-C of FIG. 4C, illustrating an initial, un-operated, condition of a pneumatic cylinder of the present invention.

FIGS. 8A, 8B, and 8C are cross-sectional views of the present invention respectively corresponding to FIGS. 6A, 6B, and 6C, illustrating an upward-pull operation of the piston of the pneumatic cylinder of the present invention, under a condition where a sleeve is in a vacuum state.

DETAILED DESCRIPTION OF THE PREFERRED EMBODIMENTS

Figure 1:
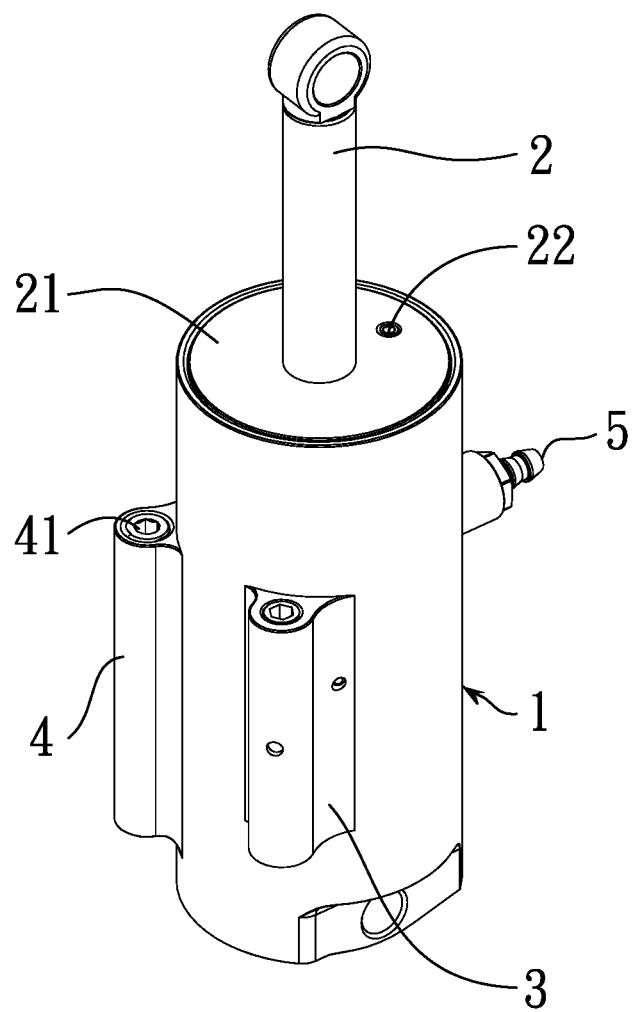
FIG. 1 is a perspective view of the present invention.

The following descriptions are exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

Generally, according to the present invention, a preferred practicable embodiment will be described hereinafter with reference to FIGS. 1-8 in order to provide a better understanding of the present invention. The present invention relates to a vacuum suction and pressure regulation cylinder, which is provided for vacuum suction and maintenance thereof between a stump and a sleeve (the sleeve being a common device in this art and not shown in the drawings) to assist a user for quick walking and comprises, structurally, a pneumatic cylinder (1), which has an outer circumferential surface on which a first one-way valve (3), a second one-way valve (4), and a sleeve one-way valve (5) that are in communication with an interior space of the pneumatic cylinder (1), are formed, the pneumatic cylinder (1) being additionally provided, in the interior thereof at a location below the sleeve one-way valve (5), a fixed division plate (11); a piston assembly (2), which comprises, mounted to a middle portion thereof, a first airtight piston (21) that comprises a flowrate regulation screw (22), so that the piston assembly (2) is slidably arranged in a through hole (111) formed in the fixed division plate (11) to allow the first airtight piston (21) to be hermetically mounted in the pneumatic cylinder (1) and the first airtight piston (21) and the fixed division plate (11) define therebetween a first air chamber (12), where the first air chamber (12) is in communication with the sleeve one-way valve (5) to conduct air from an interior space of the sleeve into the first air chamber (12); the piston assembly (2) having an end to which a second airtight piston (24) is mounted to define, in combination with the fixed division plate (11), a second air chamber (13), where the second air chamber (13) is in communication with the first one-way valve (3) to allow the first one-way valve (3) to draw in air from outside of the pneumatic cylinder (1); a third air chamber (14) being defined between the second airtight piston (24) and an internal bottom of the pneumatic cylinder (1), the second one-way valve (4) being in communication with the second air chamber (13) and the third air chamber (14), the piston assembly (2) comprising a piston air passage (23) formed therein.

Figure 2:
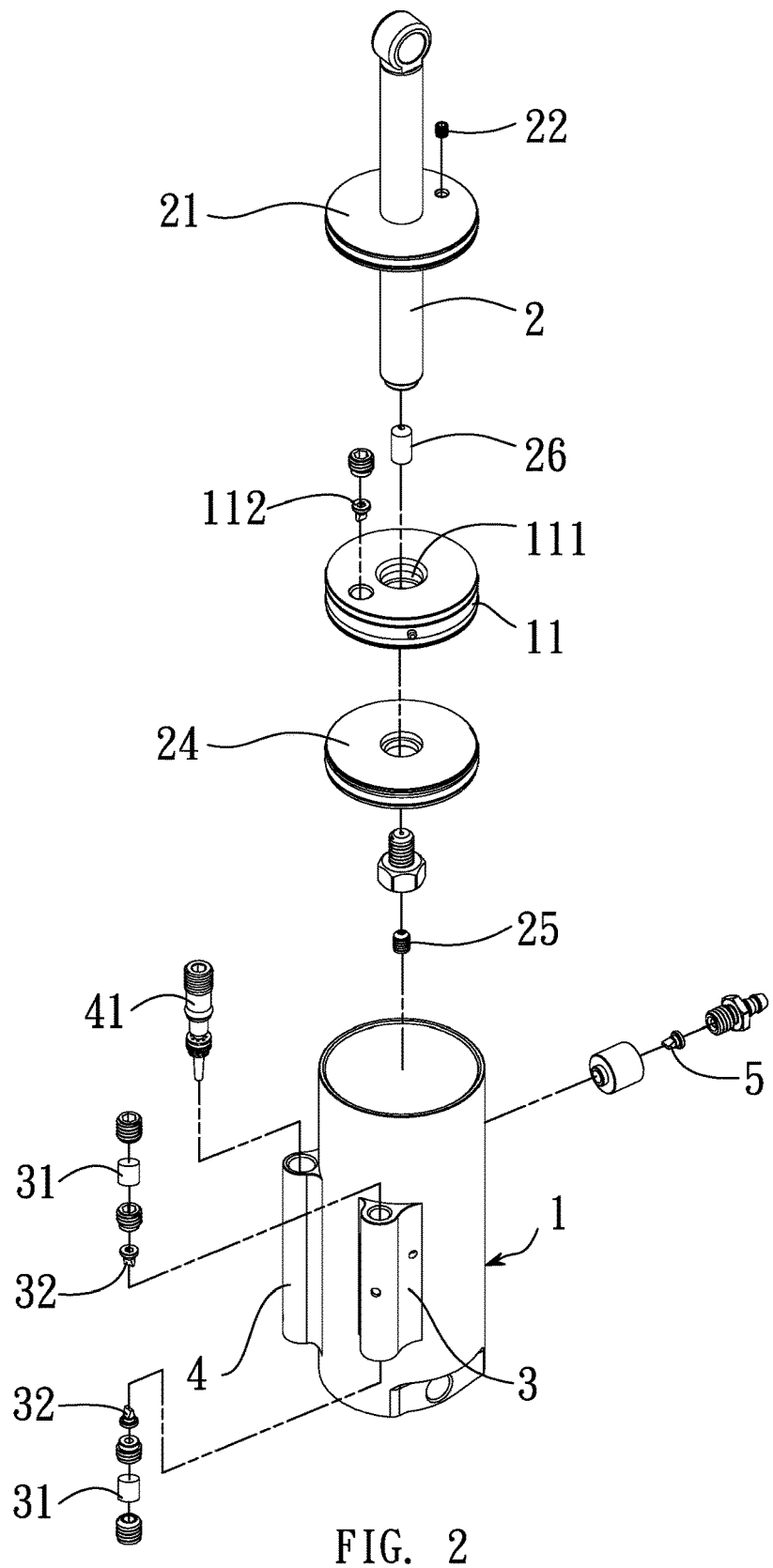
FIG. 2 is an exploded view of the present invention.
Figure 3A:
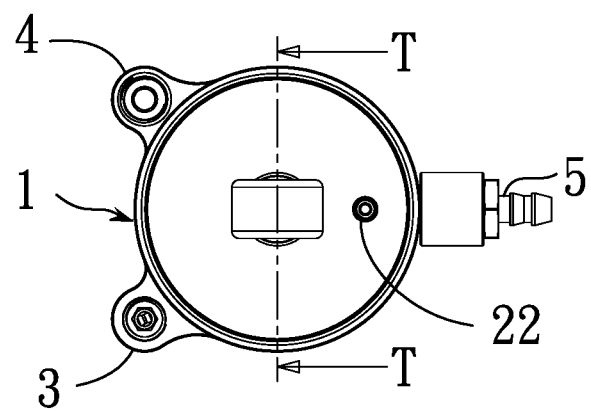
FIG. 3A is a top plan view of the present invention.
Figure 3B:
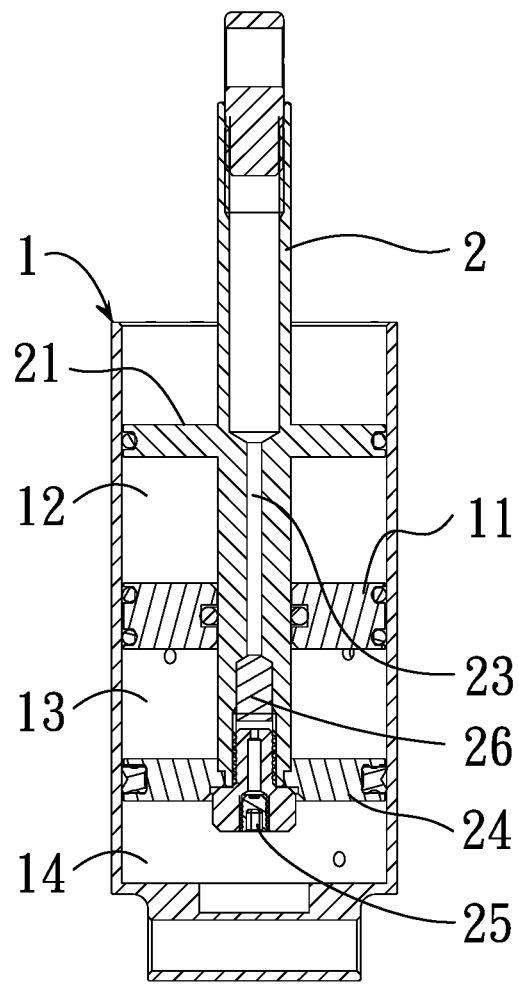
FIG. 3B is a cross-sectional view of the present invention, taken along line T-T of FIG. 3A.

Referring to FIGS. 1-3, the sleeve one-way valve (5) is generally provided for mounting to the sleeve that is attached to the user's body; two ends of the first one-way valve (3) are generally arranged to accommodate a filter core (31) and a one-way valve (32) mounted therein such that the first one-way valve (3) draw outside air into the second air chamber (13); the second one-way valve (4) comprises a one-way regulation valve (41) to allow air inside the pneumatic cylinder (1) to flow from the second air chamber (13) to the third air chamber (14).

Figure 4C:
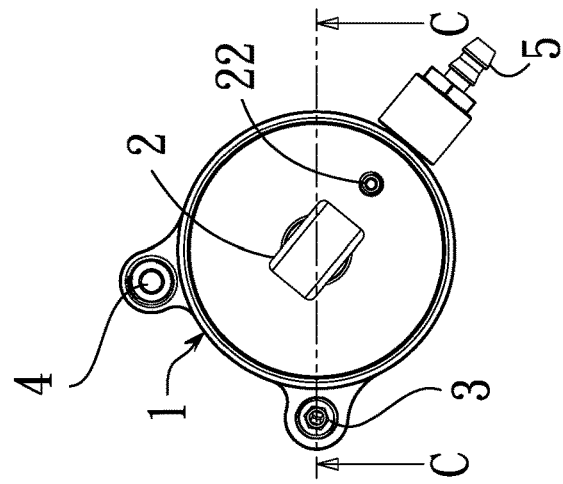
FIGS. 4A, 4B, and 4C are top plan views of the present invention set at different angles.
Figure 4B:
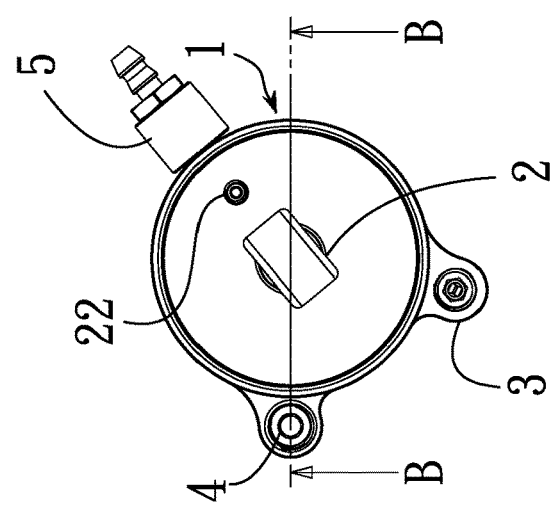
Figure 4A:
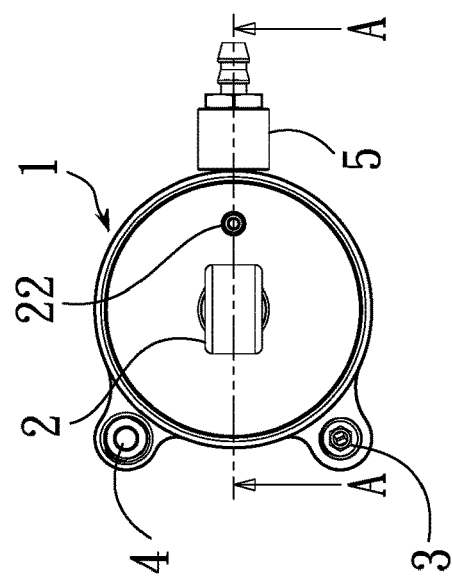

Referring to FIGS. 4A, 4B, and 4C, which are top plan views of the present invention, subsequently numbered drawings, including FIGS. 5-7, are cross-sectional views corresponding to FIGS. 4A, 4B, and 4C to illustrate an operation process of the present invention. As can be seen from FIGS. 5A, 5B, and 5C, the first air chamber (12) and the third air chamber (14) provided inside the pneumatic cylinder (1) have relatively large spaces, while the second air chamber (13) is in a compressed condition, this being an initial, un-operated state.

Figure 6A:
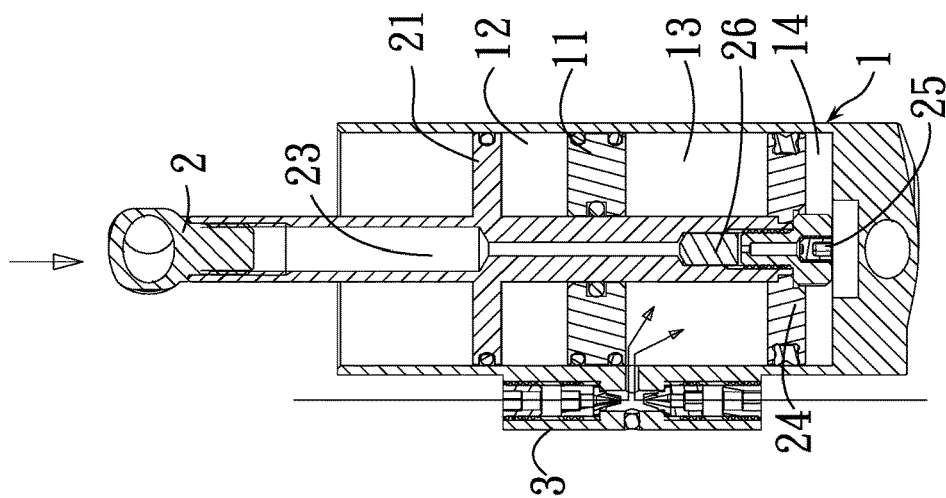
FIGS. 6A, 6B, and 6C are cross-sectional views of the present invention respectively corresponding to FIGS. 5A, 5B, and 5C, illustrating a downward-push operation of a piston of the pneumatic cylinder of the present invention.
Figure 6B:
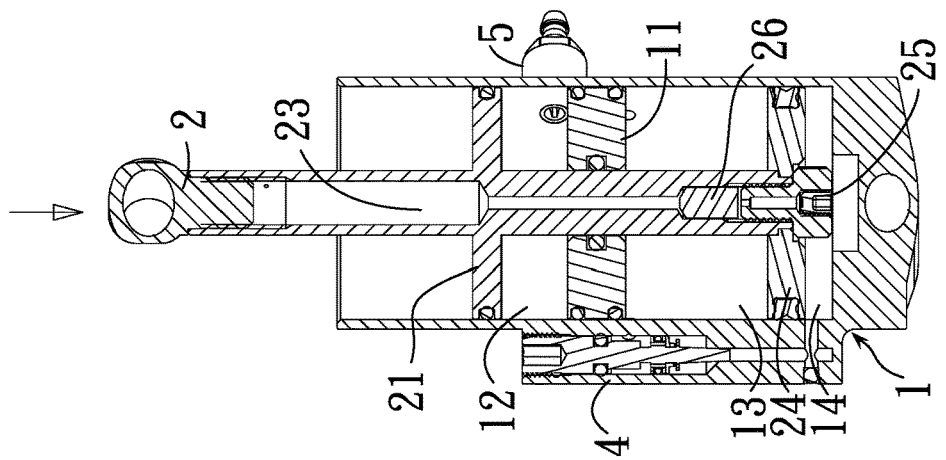
Figure 6C:
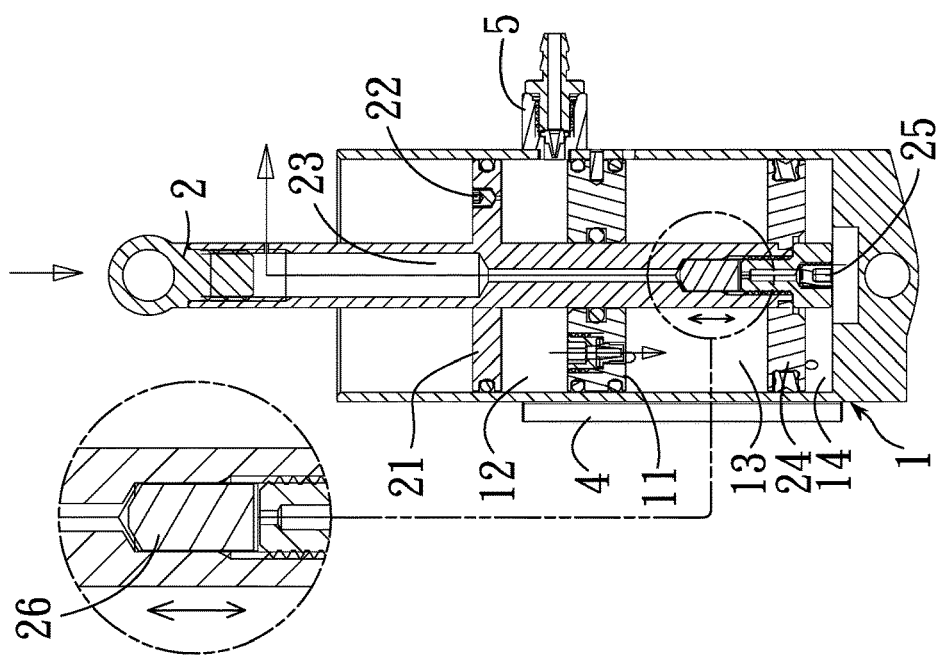

FIGS. 6A, 6B, and 6C illustrate that when a user walks and the knee bends, the piston assembly (2) receives a downward-push force and under such a condition, air inside the first air chamber (12) is compressed by the first airtight piston (21) to flow through a one-way valve (112) between the first air chamber (12) and the second air chamber (13) to enter the second air chamber (13), so that the size of the second air chamber (13) is increased, as compared to what shown in FIG. 5, so that to maintain the pressures inside the second air chamber (13), the first one-way valve (3) that is arranged on a lateral outer side of the pneumatic cylinder (3) draw air outside the pneumatic cylinder (1), in a one-way manner, into the second air chamber (13) and the third air chamber (14) is compressed by the second airtight piston (24) to expel air to the outside by flowing through a flow reduction screw (25) and a floating piston (26). At the moment when air is expelled and discharged out of the pneumatic cylinder (1), the airflow so caused may drive, in an instantaneous manner, the floating piston (26) to move so that the floating piston (26) temporarily block the piston air passage (23) and air inside the third air chamber (14) is compressed but is not allowed to flow out. A pressure so built up provides power for helping the user to walk quickly. When the pressure of the compressed air inside the third air chamber (14) gets lower down, the floating piston (26) falls down to maintain opening of the piston air passage (23) so that the user may walk in a regular way.

Figures 7A, 7B, 7C:
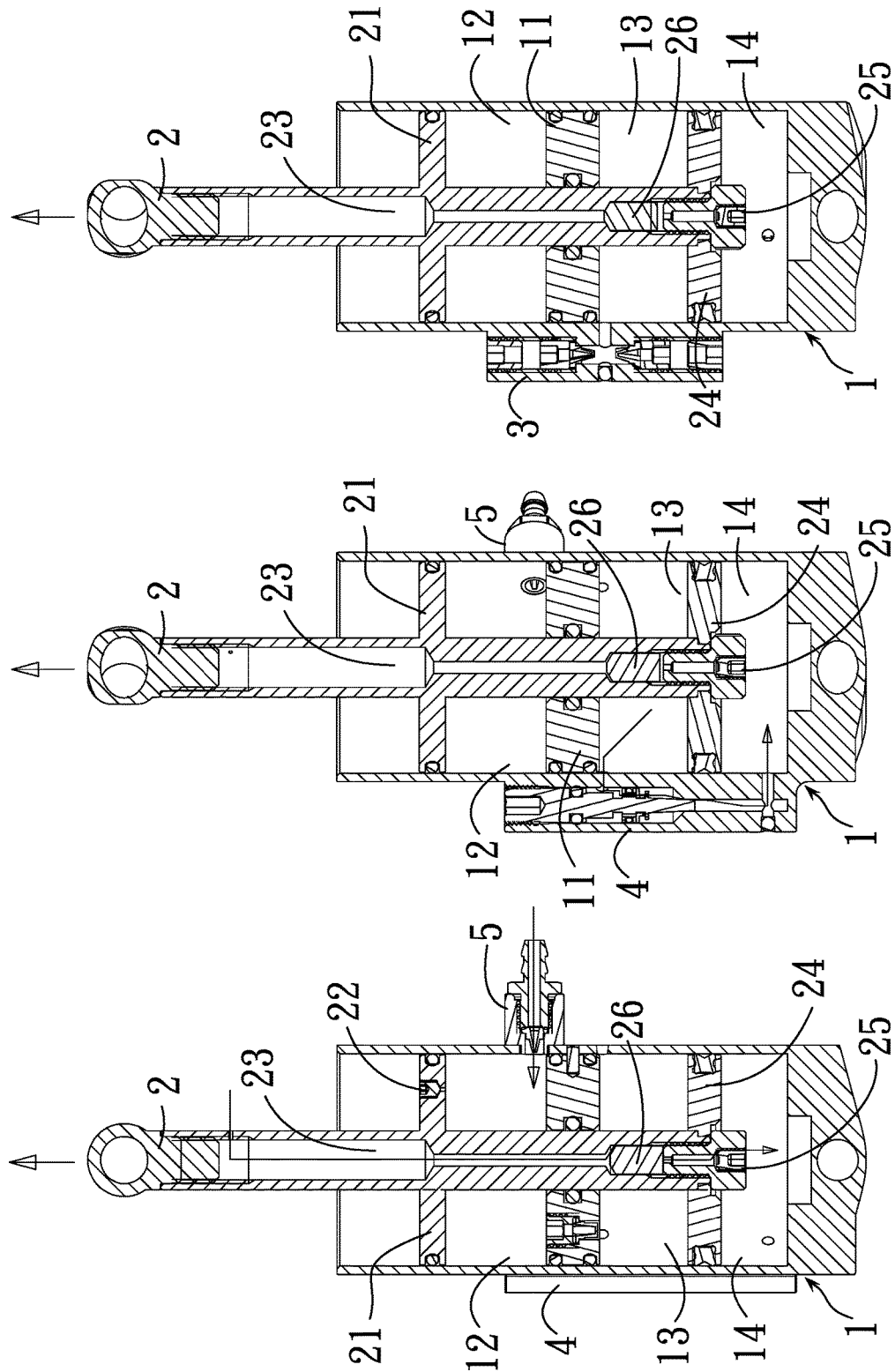
FIGS. 7A, 7B, and 7C are cross-sectional views of the present invention respectively corresponding to FIGS. 6A, 6B, and 6C, illustrating an upward-pull operation of the piston of the pneumatic cylinder of the present invention.
Figure 9:
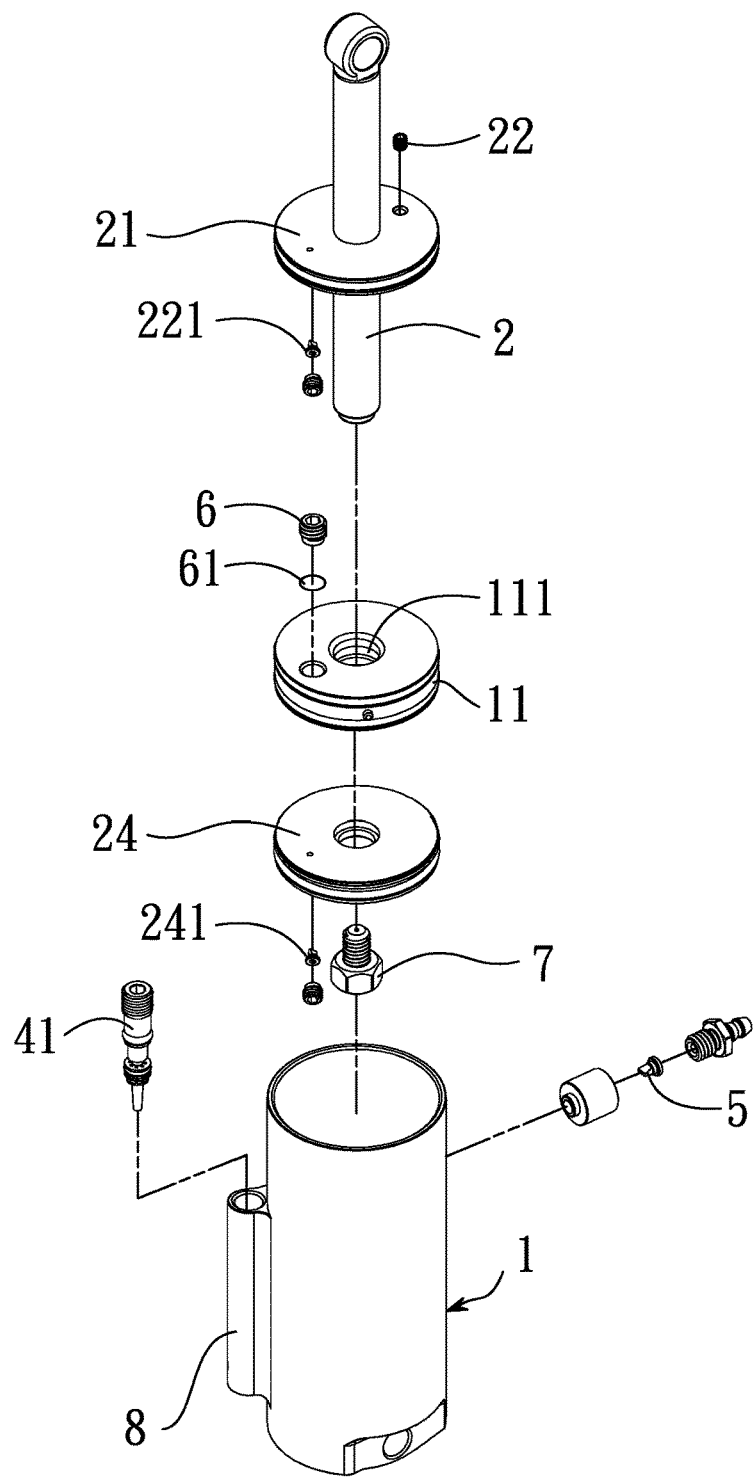
FIG. 9 is an exploded view showing another embodiment of the present invention.
Figure 10A:
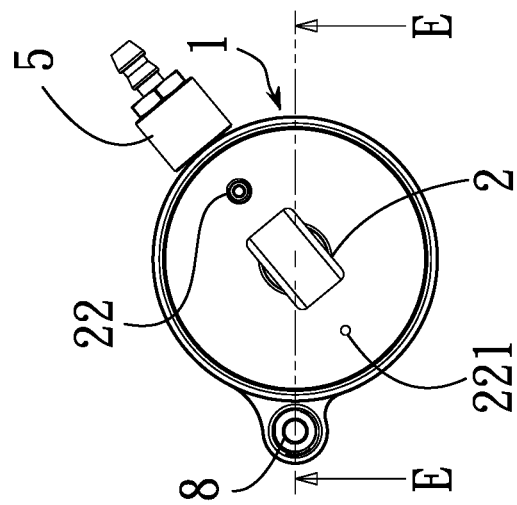
FIGS. 10A and 10B are top plan views of the present invention set at different angles.
Figure 10B:
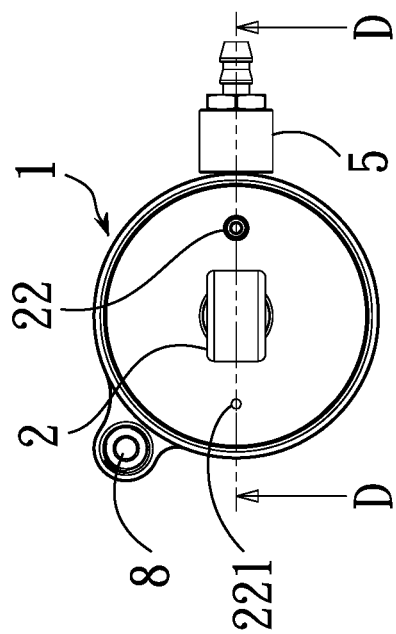
Figure 11A:
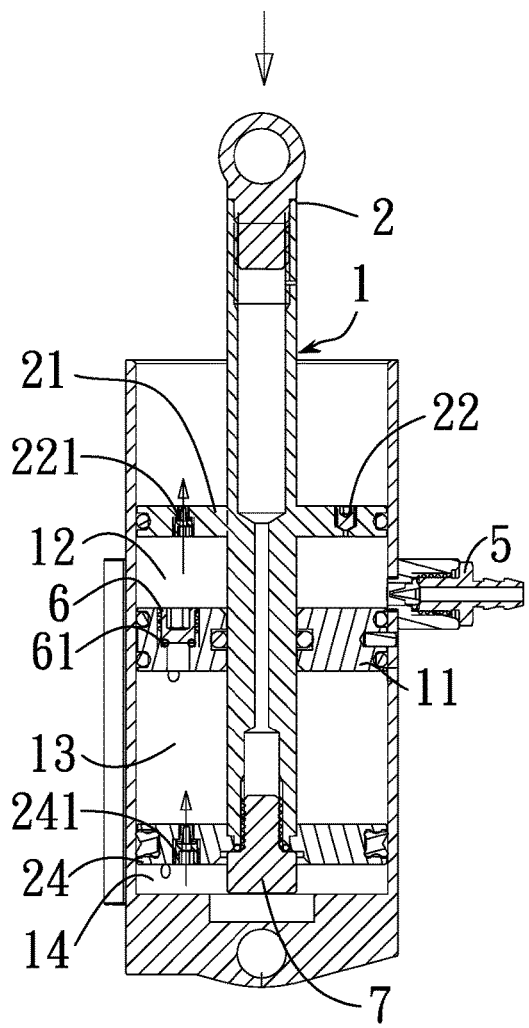
FIGS. 11A and 11B are cross-sectional views of the present invention respectively taken along line D-D of FIG. 10A and line E-E of FIG. 10B, illustrating a downward-push operation of a piston of a pneumatic cylinder of the present invention.
Figure 11B:
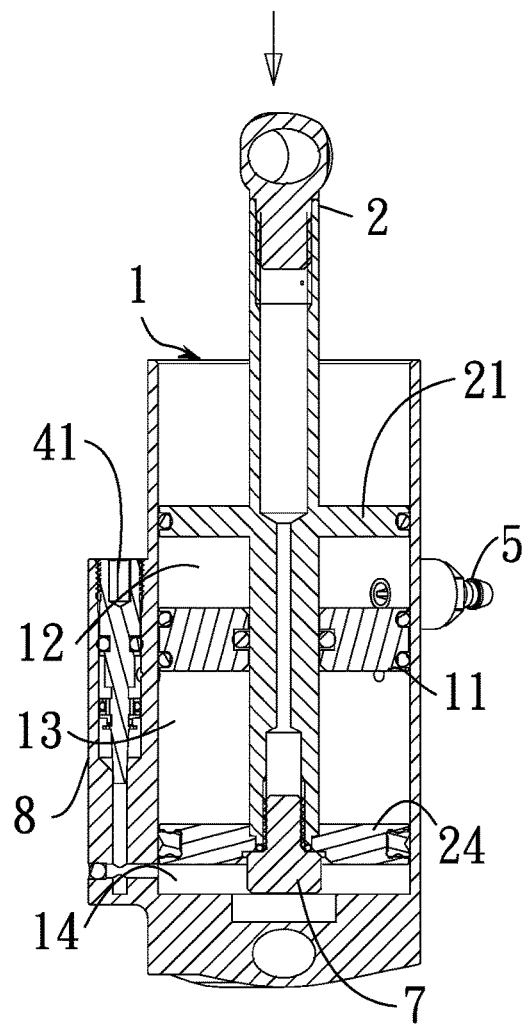
Figure 12A:
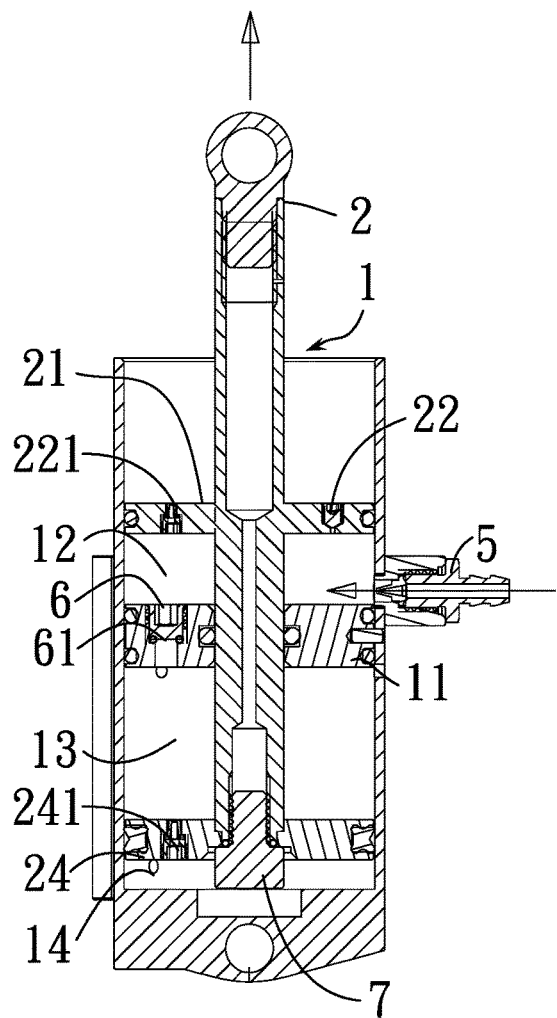
FIGS. 12A and 12B are cross-sectional views of the present invention respectively corresponding to FIG. 11A and 11B, illustrating a downward-push operation of the piston of the pneumatic cylinder of the present invention.
Figure 12B:
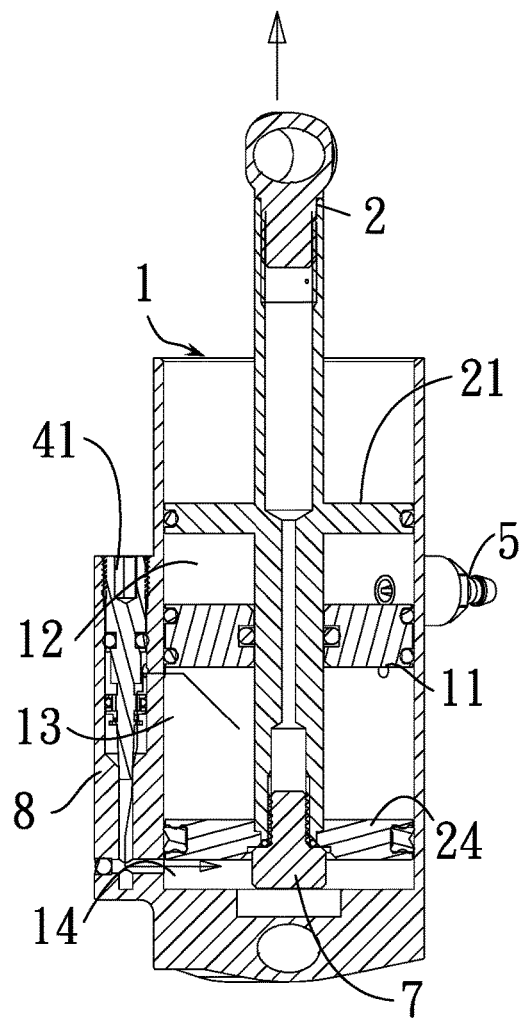

The illustrations of FIGS. 7A, 7B, and 7C provide that when the piston assembly (2) moves upwards, air inside the sleeve is guided through the sleeve one-way valve (5) into the first air chamber (12), while air inside the second air chamber (13) is driven through the one-way regulation valve (41) of the second one-way valve (4) into the third air chamber (14). The air that the third air chamber (14) receives from the second air chamber (13) or the outside air that is conducted in through the floating piston (26) and the flow reduction screw helps keeps balance of air flowing inside the pneumatic cylinder (1). To this point, the description of the operation of the pneumatic cylinder (1) is provided for the condition that the interior space of the sleeve is not in a vacuum state.

For a state where the interior space of the sleeve is in a vacuum state, the initial, un-operation condition and the knee bending condition of the user are similar to what described above with reference to FIGS. 4-6. However, when the piston assembly (2) moves upward, as shown in FIG. 8, since the interior space of the sleeve is in a vacuum state, air may flow through the flowrate regulation screw (22) into the first air chamber (12), and air inside the second air chamber (13) flows through the one-way regulation valve (41) into the third air chamber (14) so that the third air chamber (14) may receive the air from the second air chamber (13) or outside air that is drawn in through the floating piston (26) and the flow reduction screw (25) in order to maintain balance of air flowing inside the pneumatic cylinder (1).

In another embodiment of the present invention, as shown in FIGS. 9-12, minor modifications are made on the previously described structure to provide a design for a user who do not require fast walking. The modifications are as follows:

(1) The first airtight piston (21) is additionally provided with a first discharge one-way valve (221) for the purposes of allowing air contained in the first air chamber (12) to be directly discharged out of the pneumatic cylinder (1) with a movement of the piston assembly (2).

(2) The one-way valve (112) mounted in the fixed division plate (11) is closed and blocked to show a closed condition by a closure screw (6) penetrating through an 0-ring (61) so that air contained in the first air chamber (12) is not allowed to flow to the second air chamber (13) and the third air chamber (14).

(3) The second airtight piston (24) is additionally provided with a second discharge one-way valve (241) for the purposes of allowing air contained in the third air chamber (14) to flow, in a one-way manner, to the second air chamber (13) so that, together with an air-chamber one-way valve (8) connected between and in communication with the second air chamber (13) and the third air chamber (14), air is cyclically circulated between the second air chamber (13) and the third air chamber (14) according to a movement of the piston assembly (2).

The entire structure is that a pneumatic cylinder (1) has an outer circumferential surface on which an air-chamber one-way valve (8) and a sleeve one-way valve (5) that are in communication with an interior space of the pneumatic cylinder (1) are mounted and the pneumatic cylinder (1) is provided, in the interior space thereof at a location below the sleeve one-way valve (5), with a fixed division plate (11); a piston assembly (2), which comprises, mounted to a middle portion thereof, a first airtight piston (21), the first airtight piston (21) comprising a flowrate regulation screw (22) and a first discharge one-way valve (221), wherein with the piston assembly (2) slidably arranged in the fixed division plate (11), the first airtight piston (21) is hermetically contained in the pneumatic cylinder (1) and the first airtight piston (21) and the fixed division plate (11) define therebetween a first air chamber (12), the first air chamber (12) being in communication with the sleeve one-way valve (5) so as to draw air inside the sleeve into the first air chamber (12); the piston assembly (2) has an end to which a second airtight piston (24) is mounted and define, in combination with the fixed division plate (11), a second air chamber (13), the second airtight piston (24) also defining, in combination with an internal bottom of the pneumatic cylinder (1), a third air chamber (14), the air-chamber one-way valve (8) being in communication with the second air chamber (13) and the third air chamber (14), so that when the piston assembly (2) moves, an airflow is caused to change the sizes of the above mentioned air chambers and the airtight piston (24) is provided with a second discharge one-way valve (241) to allow air contained in the third air chamber (14) to flow into the second air chamber (13), so as to achieve air flow between the second air chamber (13) and the third air chamber (14) for cushioning air pressure inside the first air chamber (12) to achieve a purpose of smooth and stable walking.

The present invention provides a vacuum suction and pressure regulation cylinder of which a purpose is to allow multiple air chambers formed in the interior of the pneumatic cylinder (1) to regulate the sizes of the air chambers according to the walking speed and operations in different areas thereby making the sleeve that is attached to a stump in a vacuum state and also helping maintain the vacuum state to provide a user with a natural style of walking in a safe and secured manner.

It will be understood that each of the elements described above, or two or more together may also find a useful application in other types of methods differing from the type described above.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the claims of the present invention.

We claim:

1. A vacuum suction and pressure regulation cylinder, which is a pneumatic cylinder provided to assist pressure regulation for fast walking and induction and maintenance of vacuum between a stump and a sleeve and comprises:

a pneumatic cylinder, which has an outer circumferential surface on which a first one-way valve, a second one-way valve, and a sleeve one-way valve that are in communication with an interior space of the pneumatic cylinder, are formed, the pneumatic cylinder being additionally provided, in the interior thereof at a location below the sleeve one-way valve, a fixed division plate; a piston assembly, which comprises, mounted to a middle portion thereof, a first airtight piston that comprises a flowrate regulation screw, so that the piston assembly is slidably arranged in a through hole formed in the fixed division plate to allow the first airtight piston to be hermetically mounted in the pneumatic cylinder and the first airtight piston and the fixed division plate define therebetween a first air chamber, where the first air chamber is in communication with the sleeve one-way valve to conduct air from an interior space of the sleeve into the first air chamber; the piston assembly having an end to which a second airtight piston is mounted to define, in combination with the fixed division plate, a second air chamber, where the second air chamber is in communication with the first one-way valve to allow the first one-way valve to draw in air from outside of the pneumatic cylinder; a third air chamber being defined between the second airtight piston and an internal bottom of the pneumatic cylinder, the second one-way valve being in communication with the second air chamber and the third air chamber, the piston assembly comprising a piston air passage formed therein;

wherein the first air chamber, the second air chamber, and the third air chamber formed in the pneumatic cylinder are arranged to vary sizes of the air chambers with an airflow induced by a movement of the piston assembly so as to achieve a purpose of balance and regulation during the walking of a user and the piston air passage is provided therein with a floating piston and a flow reduction screw, so that during a process where air contained in the third air chamber is discharged out, the floating piston is instantaneously moved to close and block the piston air passage, preventing air contained in the third air chamber from being discharged out, whereby pressure of compressed air provides a power for assisting fast walking.

2. The vacuum suction and pressure regulation cylinder according to claim 1, wherein the flowrate regulation screw is operable in combination with the piston assembly being moved upward to draw in air outside the pneumatic cylinder through the flowrate regulation screw to enter the first air chamber.

3. The vacuum suction and pressure regulation cylinder according to claim 1, wherein the fixed division plate further comprises a through hole and a one-way valve, the through hole being arranged in a center of the fixed division plate to receive the piston assembly to slidably arranged therein, the one-way valve being arranged at one side of the through hole to allow air contained in the first air chamber to flow into the second air chamber.

4. A vacuum suction and pressure regulation cylinder, which is a pneumatic cylinder provided to assist pressure regulation for walking and induction and maintenance of vacuum between a stump and a sleeve and comprises:

a pneumatic cylinder, which an outer circumferential surface on which an air-chamber one-way valve and a sleeve one-way valve that are in communication with an interior space of the pneumatic cylinder are mounted and the pneumatic cylinder is provided, in the interior space thereof at a location below the sleeve one-way valve, with a fixed division plate; a piston assembly, which comprises, mounted to a middle portion thereof, a first airtight piston, the first airtight piston comprising a flowrate regulation screw and a first discharge one-way valve, wherein with the piston assembly slidably arranged in the fixed division plate, the first airtight piston is hermetically contained in the pneumatic cylinder and the first airtight piston and the fixed division plate define therebetween a first air chamber, the first air chamber being in communication with the sleeve one-way valve so as to draw air inside the sleeve into the first air chamber; the piston assembly has an end to which a second airtight piston is mounted and define, in combination with the fixed division plate, a second air chamber, the second airtight piston also defining, in combination with an internal bottom of the pneumatic cylinder, a third air chamber, the air-chamber one-way valve being in communication with the second air chamber and the third air chamber;

wherein the first air chamber, the second air chamber, and the third air chamber formed in the pneumatic cylinder are arranged to vary sizes of the air chambers with an airflow induced by a movement of the piston assembly, and the airtight piston is provided with a second discharge one-way valve to allow air contained in the third air chamber to flow into the second air chamber, allowing air to flow between the second air chamber and the third air chamber for cushioning air pressure of the first air chamber and achieving smooth walking.

\* \* \* \* \*